United States Patent
Urness et al.

(10) Patent No.: US 8,887,272 B2
(45) Date of Patent: Nov. 11, 2014

(54) MEDICAL DEVICE CUSTOMIZATION SYSTEM

(75) Inventors: Mark S. Urness, Wauwatosa, WI (US); Anders Herman Torp, Oslo (NO); Menachem Halmann, Bayside, WI (US)

(73) Assignee: General Electric Company, Schenectady, NY (US)

( * ) Notice: Subject to any disclaimer, the term of this patent is extended or adjusted under 35 U.S.C. 154(b) by 48 days.

(21) Appl. No.: 13/593,906

(22) Filed: Aug. 24, 2012

(65) Prior Publication Data
US 2014/0059677 A1     Feb. 27, 2014

(51) Int. Cl.
*G06F 12/14* (2006.01)

(52) U.S. Cl.
USPC ........... 726/21; 726/2; 726/4; 726/6; 726/15; 726/16; 726/17; 726/26; 726/29; 726/30; 726/34; 713/161; 713/165; 713/171; 713/193

(58) Field of Classification Search
USPC ................................. 726/21, 34, 15; 713/193
See application file for complete search history.

(56) References Cited

U.S. PATENT DOCUMENTS

| | | | |
|---|---|---|---|
| 7,495,552 B2 | 2/2009 | Zhang et al. | |
| 8,392,902 B2* | 3/2013 | Reinz ............................ | 717/168 |
| 2002/0077850 A1 | 6/2002 | Mcmenimen et al. | |
| 2004/0176667 A1* | 9/2004 | Mihai et al. ................... | 600/300 |
| 2007/0118397 A1* | 5/2007 | Williams et al. ................ | 705/2 |
| 2007/0129684 A1* | 6/2007 | Garbini et al. ................ | 604/171 |
| 2007/0299317 A1 | 12/2007 | Hoyme et al. | |
| 2008/0141361 A1* | 6/2008 | Balfanz ............................ | 726/17 |
| 2008/0250406 A1* | 10/2008 | Carpenter et al. ................ | 718/1 |
| 2009/0113413 A1* | 4/2009 | Reinz ............................ | 717/173 |
| 2009/0249448 A1* | 10/2009 | Choi et al. ........................ | 726/4 |
| 2009/0282244 A1* | 11/2009 | Brown ............................. | 713/168 |
| 2010/0268127 A1* | 10/2010 | Lockhart ............................ | 601/2 |
| 2010/0292556 A1 | 11/2010 | Golden | |
| 2010/0298662 A1 | 11/2010 | Yu et al. | |
| 2011/0137156 A1* | 6/2011 | Razzaque et al. ............. | 600/424 |
| 2011/0179136 A1* | 7/2011 | Twitchell, Jr. ................. | 709/217 |
| 2011/0289497 A1* | 11/2011 | Kiaie et al. ..................... | 717/171 |
| 2011/0301454 A1* | 12/2011 | Chono ........................... | 600/425 |

(Continued)

FOREIGN PATENT DOCUMENTS

| | | |
|---|---|---|
| EP | 1199984 A1 | 5/2002 |
| WO | 03096154 A2 | 11/2003 |

OTHER PUBLICATIONS

Greenbaum et al, TiArA: A Virtual Appliance for the Analysis of Tiling Array Data, PLosOne, Apr. 2010, vol. 5, issue 4. pp. 1-6.*

(Continued)

*Primary Examiner* — Luu Pham
*Assistant Examiner* — Jenise Jackson
(74) *Attorney, Agent, or Firm* — Rathe Lindenbaum LLP

(57) ABSTRACT

A medical device customization system and method comprising medical device that receives signals from a biological probe having an operational parameter and that stores data based on the signals in a memory. The medical device receives a custom application and establishes a virtual machine to run the custom application.

24 Claims, 7 Drawing Sheets

(56) References Cited

U.S. PATENT DOCUMENTS

| | | |
|---|---|---|
| 2012/0079265 A1 | 3/2012 | Ferren |
| 2012/0084780 A1 | 4/2012 | Pasternak |
| 2012/0117558 A1 | 5/2012 | Futty et al. |
| 2013/0172696 A1* | 7/2013 | Riesinger .................. 600/309 |
| 2013/0184587 A1* | 7/2013 | Eom et al. ................. 600/443 |
| 2013/0218978 A1* | 8/2013 | Weinstein et al. .......... 709/205 |
| 2013/0232114 A1* | 9/2013 | Mortazavi et al. .......... 707/634 |
| 2013/0247194 A1* | 9/2013 | Jha et al. ................... 726/23 |
| 2013/0326639 A1* | 12/2013 | Droste et al. .............. 726/28 |
| 2014/0173058 A1* | 6/2014 | Twitchell, Jr. ............. 709/219 |

OTHER PUBLICATIONS

Vonesch et al, The Colored Revolution of Bioimaging, IEEE, May 2006, pp. 1-6.*

* cited by examiner

| AUTHORIZATION KEY | AUTHORIZATION LEVEL | ACCESS/PERMISSION |
|---|---|---|
| AK 1 | 1 | ALL BASE DATA ACCESS (READ) |
| AK 2 | 2 | ALL BASE DATA ACCESS (READ & WRITE) |
| AK 3 | 3 | SUBJECT OF BASE DATA ACCESS (READ) |
| AK 4 | 4 | SUBJECT OF BASE DATA ACCESS (READ & WRITE) |
| AK 5 | 5 | CPU USAGE - BAVM DORMANCY |
| AK 6 | 6 | CPU USAGE - BT DORMANCY |
| AK 7 | 7 | OPERATIONAL PARAMETER ACCESS LEVEL 1 |
| AK 8 | 8 | OPERATIONAL PARAMETER ACCESS LEVEL 2 |

FIG. 3

MEDICAL DEVICE CUSTOMIZATION SYSTEM

BACKGROUND

A medical device may utilize a biological probe operating under an operational parameter to interact with a patient and to generate data based on signals from the biological probe. Although different users may prefer different output formats or uses for the data or different settings for the operational parameter, customization for different preferences may be costly, may detrimentally reduce performance of the medical device and may be difficult to provide without rendering the original data or the operational parameter susceptible to undesirable alterations.

BRIEF DESCRIPTION OF THE DRAWINGS

FIG. 3 is a chart listing examples of authorization keys and authorization levels use in the medical device customization system of FIG. 2.

DETAILED DESCRIPTION OF THE EXAMPLE EMBODIMENTS

Figure 1:
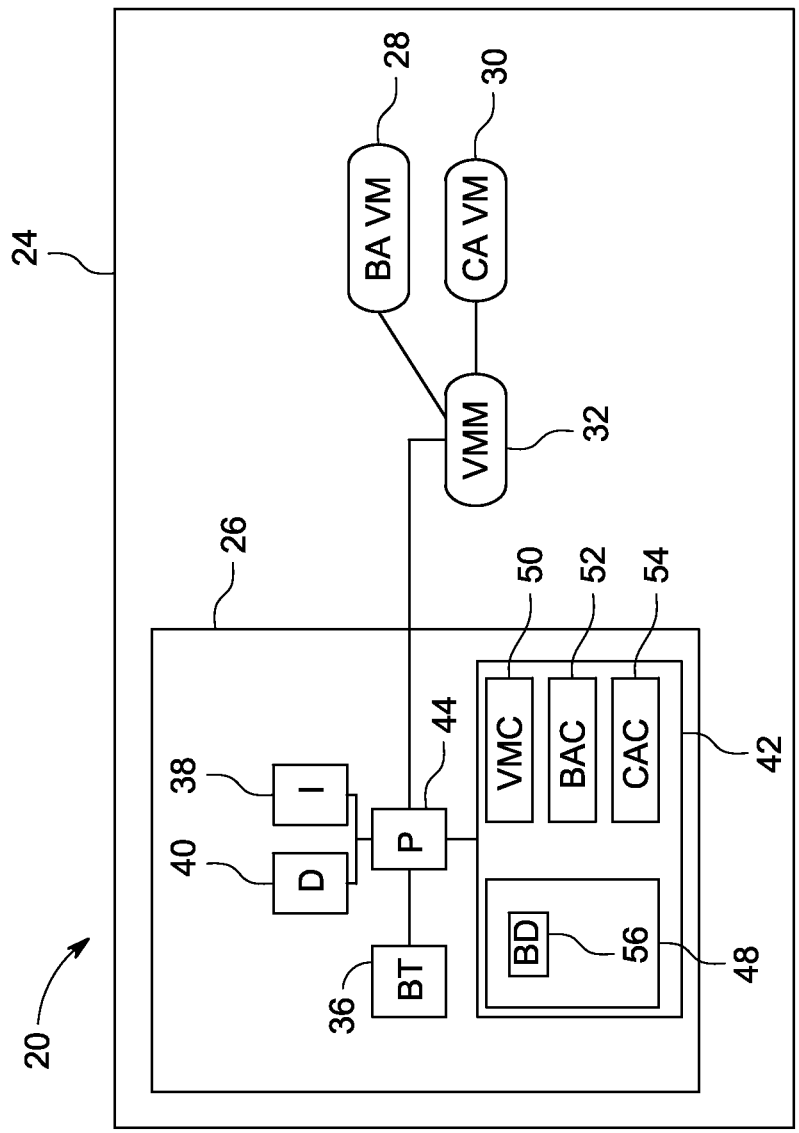
FIG. 1 is a schematic illustration of an example medical device customization system.

FIG. 1 schematically illustrates an example medical device customization system 20. As will be described hereafter, system 20 facilitates customization of a medical device to address specific needs of a customer or end user of the medical device. System 20 facilitates such customization of the medical device in a cost-effective manner while preserving operational and data integrity of the medical device.

System 20 comprises a medical device 24 which includes physical hardware 26, a base application virtual machine 28, a custom application virtual machine 30 and a virtual machine manager 32. Physical hardware 26 comprises the electronic hardware of medical device 24 which is utilized by base application virtual machine 28 and at least sometimes by custom application virtual machine 30. Physical hardware 26 comprises biological probe 36, input 38, display 40, memory 42 and processing unit 44.

Biological probe 36 comprises a device that interacts with a patient to sense one or more biological characteristics of the patient. In one implementation, biological probe 36 may merely sense such characteristics without affecting or impacting such characteristics. In another implementation, biological probe 36 may sense such biological characteristics of the patient as the patient is operated upon using the medical device, wherein the biological probe 36 provides feedback during surgery or operation. Examples of biological probe 36 include, but are not limited to, an ultrasound probe of an ultrasound diagnostic medical device. Signals produced by biological probe 36 are transmitted to processing unit 44 for analysis, output and/or data storage.

Input 38 comprises a component of medical device 24 by which selections, commands or instructions are input to medical device 24. Examples of input 38 comprise a touchpad, a touch screen, a keypad, a keyboard, a mouse, a stylus, a microphone with speech recognition software, pushbuttons, slider bars and the like. In one implementation, input 38 may comprise a port for connection to a wired connection to an external input device or a wireless card or antenna for a wireless connection to an external input device. In some implementations, input 38 may be omitted.

Display 40 comprises a component of medical device 24 by which the data (raw or processed) from or based upon signals from biological probe 36 may be output or presented to a caretaker or physician. Examples of display 40 include, but are not limited to, a screen, monitor, LCD display, LED panel or display and the like. In one implementation, display 40 may comprise a touch screen, wherein display 40 also serves as input 38. In some implementations, display 40 is incorporated as part of the body or housing of medical device 24. In another implementation, display 40 is a separate unit connected to or in communication with central processing unit 44. In yet another implementation, display 40 may be omitted or may be separately provided as part of an independent electronic device, such as a personal data assistant, tablet, IPAD, IPOD or other external device connected to or in communication with medical device 24.

Memory 42 comprises one or more non-transient computer-readable mediums or persistent storage devices by which computer readable programs or code and data may be stored and accessed. Memory 42 comprises data storage portion 48, virtual machine code 50, base application code 52 and custom application code 54. Data storage portion 48 comprise that portion of memory 42 reserved for storing base data 56. Base data 56 comprises raw data received from biological probe 36 or data produced by base application virtual machine 28 according to instructions contained in base application code 52. Base data 56 comprises data produced by medical device 24 absent any customization through one or more custom applications. Base data 56 comprises data which may be further manipulated or processed by one or more custom applications to satisfy a customer's particular objectives.

Virtual machine code 50 comprises software or programming code directing processor 44 to generate and operate a virtual machine manager 32. Base application code 52 comprises software or programming code facilitating the generation and operation of base application virtual machine 28. Custom application code 54 comprises software or programming code facilitating the generation and operation of custom application virtual machine 30.

Processing unit 44 comprises one or more processing units per carry out instructions contained in virtual machine code 50, base application code 52 and custom application code 54 to generate and operate base application virtual machine 28, custom application virtual machine 30 and virtual machine manager 32. For purposes of this application, the term "processing unit" shall mean a presently developed or future developed processing unit that executes sequences of instructions contained in a memory. Execution of the sequences of instructions causes the processing unit to perform steps such as generating control signals. The instructions may be loaded in a random access memory (RAM) for execution by the processing unit from a read only memory (ROM), a mass storage device, or some other persistent storage. In other embodiments, hard wired circuitry may be used in place of or in combination with software instructions to implement the functions described. For example, processing unit 44 may be embodied as part of one or more application-specific integrated circuits (ASICs). Unless otherwise specifically noted, the processing unit 44 (sometimes referred to as a controller) is not limited to any specific combination of hardware circuitry and software, nor to any particular source for the instructions executed by the processing unit.

Base application virtual machine 28 comprises an isolated operating system installation implemented through software or hardware virtualization. Base application virtual machine 28 comprises an application virtual machine, running as a normal application inside the host operating system of medical device 24 and supporting or carrying out base processes of medical device 24 according to base application code 52. For example, base application virtual machine 28 controls the operational parameters for biological probe 36. Base application virtual machine 28 processes signals from biological probe 28 and controls the storage of such raw data signals from biological probe 36 in storage portion 48 of memory 42. Base application virtual machine 28 may further process and analyze such signals from biological probe 36 to store additional data derived from such signals in storage portion 48 of memory 42. Base application virtual machine 28 further controls the display of data on display 40 and user interfaces for the control of biological probe 36 and display 40 through input 38. For example, base application virtual machine 28 may control how data is presented or what format is used when presenting data or other information on display 40 or what graphical user interfaces or icons are presented on a touch screen of input 38. Base application virtual machine 28 has unlimited access to hardware 26 and data stored in memory 42.

Custom application virtual machine 30 comprises an isolated operating system installation implemented through software or hardware virtualization. Custom application virtual machine 30 comprises an application virtual machine, running as a normal application inside the host operating system of medical device 24 and supporting or carrying out base processes of medical device 24 according to custom application code 54. Custom application virtual machine 30 provides additional features or modifies operation of medical device 24 according to an end user's objectives. For example, custom application virtual machine 30 may provide further processing or analysis of the base data 56 stored by base application virtual machine 28 in storage portion 48 of memory 42, providing or forming new post processing data or new conclusions derived from base data 56. Custom application virtual machine 30 may also provide different formats (presentation styles, screen layouts, graphs, color coding and the like) for the output of base data 56. In some implementations, custom application virtual machine 30 may alter the operational parameters of biological probe 36, altering the settings for transducer 36 or driving transducer 36 to obtain additional measurements. Custom application virtual machine 30 provides customized operation of medical device 24. In one implementation, virtual machine 28, 30 are implemented with JAVA programming language employing a JAVA virtual machine.

Virtual machine manager 32, sometimes referred to as a hypervisor, manages the execution of base application virtual machine 28 and custom application virtual machine 30. Virtual machine manager 32 is operates according to virtual machine code 50 and serves as an interpreter implementing base application virtual machine 28 and custom application virtual machine 30. Virtual machine manager 32 manages utilization of and access to various components of hardware 26 and base data 56 by virtual machines 28, 30.

Because custom applications defined by custom application code 54 operate through virtual machine 30, system 20 may be updated or customized to accommodate new and different environments, user demands, and advances. At the same time, because virtual machine 30 implements such customization, system 20 may offer such customization while maintaining integrity of the original base application and the original (potentially FDA approved) operation of medical device 24 and biological probe 36. In other words, the risk that a custom application may undesirably alter the original intended operation of medical device 24 or may undesirably destroy or alter based data 56 is reduced.

Figure 2:
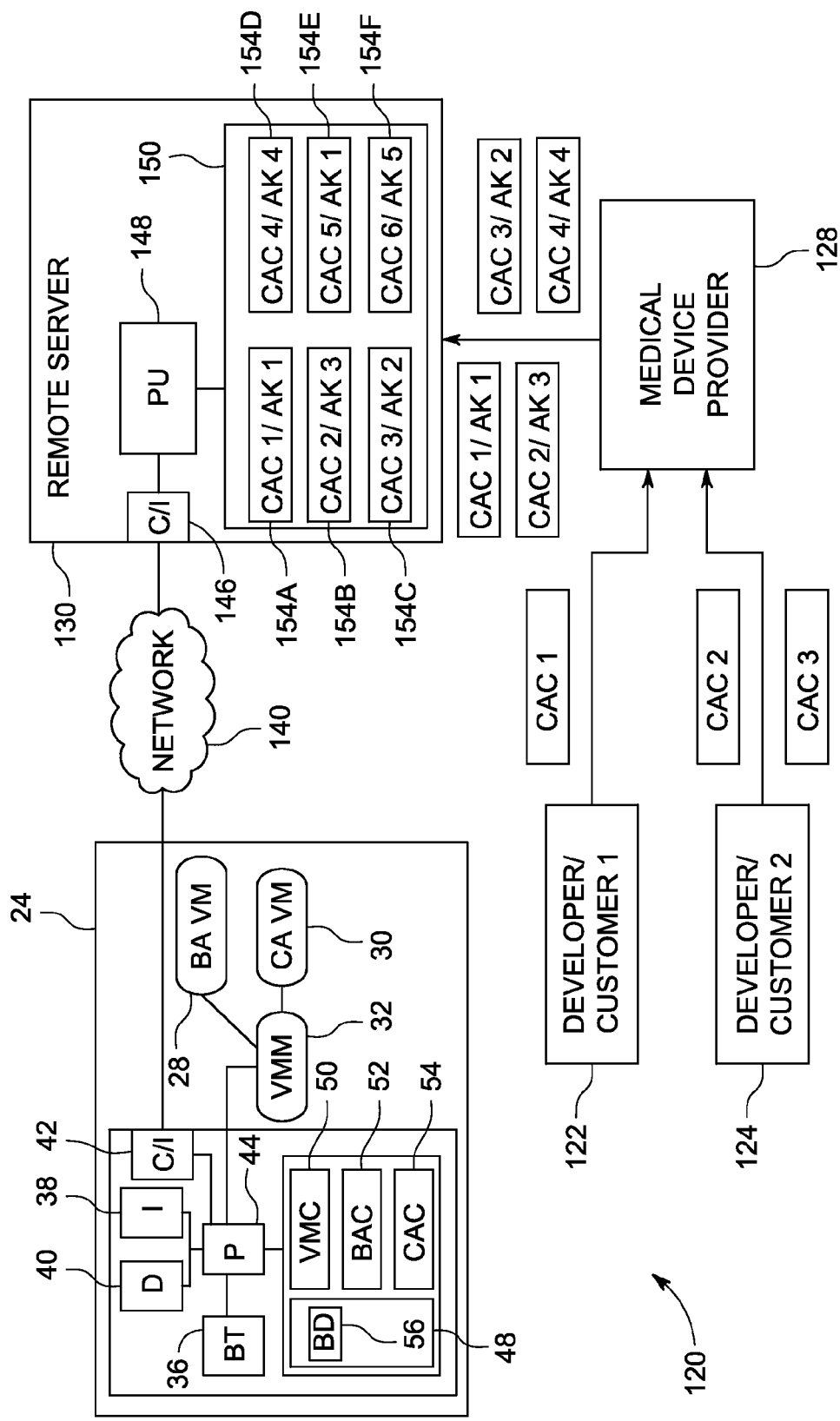
FIG. 2 is a schematic illustration of another example medical device customization system.

FIG. 2 schematically illustrates medical device customization system 120, another implementation of system 20. Like system 20, system 120 allows a medical device to be upgraded or customized while maintaining the integrity of the underlying or base medical device operation and data through the use of a virtual machine. System 120 offers additional protection to further preserve, control or manage the integrity of the base data and basic operation parameters of the medical device. As will be described hereafter, system 120 implements authorization or access protocols to manage or restrict what alterations may be carried out by a custom application.

System 120 comprises medical device 24, developer/customers 122, 124, medical device provider 128 and remote server 130. Medical device 24 is described above respect to system 20. Those elements of system 120 which correspond to elements of system 20 are numbered similarly.

Developer/customers 122, 124 comprise distinct companies, entities or individuals which are also distinct from the provider manufacturer of medical device 24 and who develop customized applications for medical device 24. Such developer/customers 122, 124 may be the end-users of medical device 24 (those who purchase advice 24 from provider 128) or may be third parties who develop such custom applications on behalf of the end-user of medical device 24. In the example illustrated, developer/customer 122 has developed a custom application CAC1 for medical device 24 while developer/customer 124 has developed to custom applications CAC2 and CAC3 for medical advice 24. Such custom applications are submitted to medical device provider 128 for approval and possible distribution.

Medical device provider 128 comprises a manufacturer, developer or creator of medical device 24. Provider 128 may comprise an entity which developed base application code 52 or which obtained regulatory approval for the use and operation of medical device 24. Provider 128 may generate, develop or create additional custom applications, such as custom application CAC4. Provider 128 receives custom applications developed by outside entities, such as from developer/customers 122, 124 and reviews such independently developed and submitted custom applications. Provider 128 determines what level of authority or access to hardware 26 (including base data 56 stored on such hardware 26) of medical device 24 to assign or grant to each particular custom application prior to its distribution or storage on medical device 24. In the example illustrated, provider 128 (including entities to which such authorization granting responsibilities have been delegated) assigns an encrypted authorization key to each custom application prior to making the custom application available for distribution via remote server 130. In the example illustrated, provider 128 assigns custom application CAC1 with an authorization key AK1, assigns custom application CAC2 with an authorization key AK3, assigns custom application CAC3 with an authorization key AK2 and assigns custom application CAC4 (developed by provider 128) with an authorization key AK4.

Authorization keys AK comprising encrypted passwords, authorization codes and the like which correspond to and indicate an authorization level that has been granted to the particular custom application. Such authorization keys AK are embedded in, attached to or associated with the software or programming code of the custom application by provider 128 such that such authorization keys AK accompany the custom application during its distribution.

FIG. 3 is a chart illustrating examples of authorization keys that may be assigned to particular custom applications. As shown by FIG. 3, the example authorization key AK1 corresponds to authorization level 1 which provides a custom application access or permission to read and utilize the entire set of base data 56 stored in memory 42. In other words, a custom application provided with authorization key AK1 will be allowed to perform post processing on any and all base data 56. Integrity is original base data 56 is maintained.

The example authorization key AK2 corresponds to an authorization level 2, wherein the custom application provided with such an authorization key may not only access all of the base data 56 for reading such data, but may also write or change such data in memory 42. With such access, raw data or results from initial processing of such raw data by base application virtual machine 28 may be corrected or revised by a custom application.

The example authorization key AK3 corresponds to an authorization level 3. Authorization key AK3 is similar to authorization key AK1 except that the custom application assigned authorization key AK3 has read access to just a subset or portion of base data 56. In other words, read access to base data 56 by the custom application is limited such that not all of base data 56 is obtainable or usable by the custom application. Authorization key AK4 is similar to authorization key AK2 except that the custom application assigned authorization key AK4 has read/write access to just a subset or portion of base data 56. In other words, read/write access to base data 56 by the custom application is limited such that not all of base data 56 may be obtained or altered by the custom application.

Authorization key AK5 corresponds to an authorization level 5 wherein the custom application virtual machine 30 carrying out the custom application has a restricted use of processing unit 44. In the example illustrated, the custom application may only be carried out when the base application virtual machine is not running or is in a state of dormancy. Authorization key AK5 reserves processor 44 for use by base application virtual machine 28. Authorization key AK5 prevents processor 44 from becoming overloaded with computational tasks from the custom application and preserves the operational responsiveness of the base application of medical device 24.

Authorization key AK6 corresponds to an authorization level 6 wherein the custom application virtual machine 30 carrying out the custom application has restricted use of processor 44 based upon whether or not biological probe 36 is transmitting signals. In the example illustrated, authorization key AK6 permits the customize application to utilize resources of processor 44 except when processor 44 is receiving signals from biological probe 36. In other words, authorization key AK6 permits use of processor 44 by the custom application (custom application virtual machine 30) when the biological probe 36 is not being used or is dormant. For example, in one implementation where biological transistor 36 comprises an ultrasound probe, a custom application assigned with authorization key AK6 may permitted to use processor 44 when the ultrasound probe (serving as the biological adjusted 36) is not in a scanning state. Authorization key AK6 gives priority to the receipt and initial processing of signals from biological probe 36 over any functions to be carried out on processor 44 by a custom application.

Authorization keys AK7 and AK8 correspond to authorization levels 7 and 8, respectively. Authorization keys AK7 and AK8 provide the custom applications to which they are assigned the authorization to modify operational parameters of medical device 24. In one implementation, authorization key AK7 gives a custom application authorization or permission to alter a first operational parameter of medical device 24. Authorization key AK8 gives a custom application authorization or permission to alter a second different operational parameter of medical device 24. For example, a particular authorization key AK7 may allow a custom application to alter a frequency at which biologic transducer 36 senses information while a particular authorization key AK7 allows a custom application to alter sensitivity of the biological probe 36. In another implementation, authorization key AK7 provides a custom application with authorization or permission to alter a first operational parameter of medical device 24 within a first range of values or settings while authorization key AK8 provides a custom application with authorization or permission to alter the first operational parameter of medical device 24 within a second different range of values or settings. For example, a particular authorization key AK7 may permit a custom application to alter a sensitivity of biological probe 36 to a new sensitivity within a first range of sensitivity levels while a particular authorization key AK8 may permit a custom application to alter a sensitivity of biological probe 36 three new sensitivity within a second range larger than the first range of sensitivity levels. In other implementations, a greater or fewer of such authorization keys may be attached to a custom application by provider 128 or another entity. Other authorization keys having other restrictions or other access permissions may be used. Custom applications may be assigned more than one authorization key providing different access capabilities. In some implementations, the permissions provided by a plurality of the above-described authorization keys may be combined and collectively indicated a different authorization key. Although the above describes authorization keys or authorization levels as being signed integer numbers, such authorization levels may be designated by any arrangement of alpha-numeric characters, graphics, codes (such as two-dimensional, three-dimensional and other bar codes) and the like.

As shown by FIG. 2, in the example illustrated, the custom applications to which authorization keys have been assigned are distributed by remote server 130. Remote server 130 comprises a computer server accessible through network 140. Network 140 may comprise a wide area network, such as the Internet, or may comprise a local area network. Remote server 130 facilitates transmission or downloading of custom applications for storing and installation on one or more medical devices 24. Remote server 130 is remotely located from medical devices 24. Remote server 130 enables otherwise identical medical devices 24 to be customized with custom applications retrieved from remote server 130 as desired by an end-user of the particular medical device 24. In one implementation, remote server 130 establishes and manages a website on the Internet by which authorized end users may download custom applications for their medical devices 24.

Remote server 130 comprises a computer serving requests of clients for the download of custom applications. Most server 130 comprises communication interface 146, processing unit 148 and memory 150. Communication interface 146 comprises a device by which remote server 130 communicates with remote clients through network 140. Such communication may be in a wired or wireless fashion. In one implementation, medication interface 146 comprises a modem.

Processing unit 148 comprises one or more processing units configured to generate control signals according to instructions contained in a memory providing an interface by which clients may access and select or download custom application stored in memory 150. Memory 150 comprises a non-transient computer-readable medium or persistent storage device in which custom applications and their associated authorization keys are stored for distribution or retrieval. In the example illustrated, memory 150 is illustrated as storing six custom applications and their associated authorization keys (custom application and authorization key packages 154A-154F. In other implementations, memory 50 may store and make available a greater or fewer of such custom applications and associated authorization keys.

Figure 4:
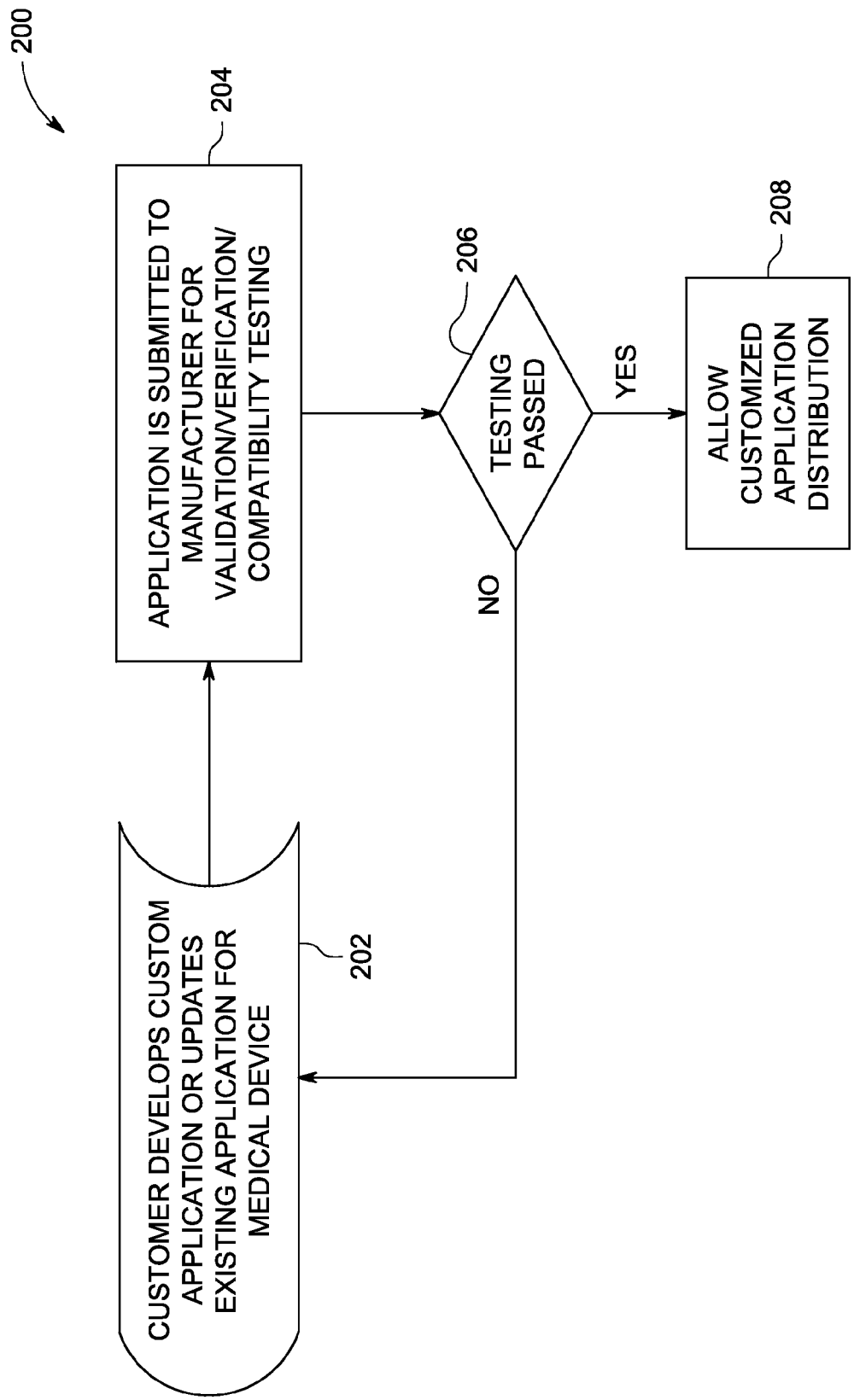
FIG. 4 is a flow diagram of an example method for generating a custom application for use in the system of FIG. 2.

FIG. 4 is a flow diagram illustrating an example method 200 for the creation or development of custom applications for medical device 24 and the assignment of authorization keys. As indicated by step 202, the developer/customer develops custom applications or updates (custom application 54) for an existing application (base application 52) on medical device 24. As indicated by step 204, the generated custom application 54 is submitted to the medical device provider 128 (manufacturer) for validation/verification/compatibility testing. In one implementation, the provider 128 determines whether such alterations impact a previous FDA approval for use of the medical device 24. In other implementations, provider 128 may evaluate the submitted custom application 54 pursuant to other criteria such as safety, reliability, performance and the like. As indicated by steps 206 and 208, upon approval by the provider 128, the custom application is authorized for distribution. In one implementation, provider 128 assigns an authority level to the custom application. In one implementation provider 128 associates an encrypted authorization key indicating the level of authority or access that the custom application will have to the hardware 26 and stored based data 56 of medical device 24. In one implementation, the encrypted authorization key is not disclosed to the customer or developer, inhibiting any circumvention of such security measures by provider 128. Alternatively, if the custom application is not approved, the custom application is not distributed and is not assigned any authorization key, effectively inhibiting its use on medical device 24.

Figure 5:
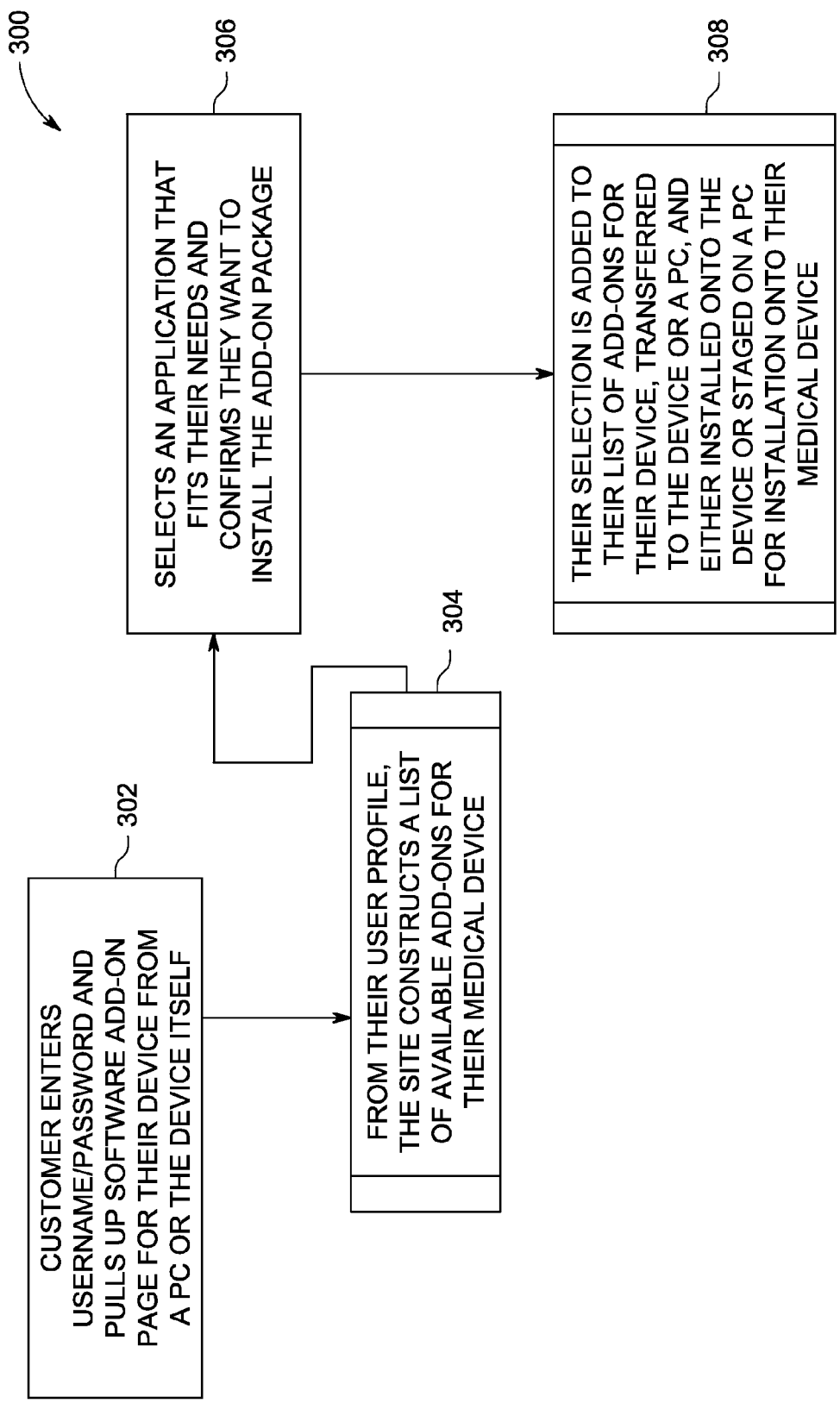
FIG. 5 is a flow diagram of an example method for distributing a custom application for use in the system of FIG. 2.

FIG. 5 is a flow diagram of an example method 300 for the distribution of the custom application. As indicated by step 302, the end-user of medical device 24 (the customer) opens the website provided by remote server 130 through a browser and enters his or her username and password to pull up a web page or portal to remote server 130. As indicated by step 304, using the entered username and password, remote server 130 accesses a profile for the user and/or an identification of medical devices (previously registered with remote server 130) associated with the person. Based upon the user profile or the medical device or devices associated with the person, remote server 130 displays a list of available custom applications for the medical device 24. In other implementations, the person may identify the medical device 24, wherein remote server 130, on the webpage, lists all custom applications for the identified medical device 24. The webpage may be displayed on a display of the medical device itself, display 40, or on another computing or display device.

As indicated by step 306, the webpage provided by remote server 130 may display and offer a search function, wherein the end-user customer may search for particular custom applications having particular features, particular characteristics or particular levels of access to hardware 26 and data 56 of medical device 24. Based on such needs, remote server 130 may select one or more custom applications from its repository that best fit the needs of the end-user or the search criteria. Remote server 130 then prompts the end-user customer to select one or more of the display custom applications for download.

As indicated by step 308, the custom applications are downloaded. In one implementation, the selected custom application(s) are downloaded directly to the medical device through a communication interface 42 (shown in FIG. 2) of the medical device 24. In another implementation, the selected custom applications may be downloaded to a separate computing device, wherein the downloaded custom applications are subsequently transferred to the medical device in a wired or wireless fashion. The downloaded custom applications may be stored in memory 42 (identified as custom application code 54) and may be installed for subsequent use of medical device 24. In some implementations, the custom applications may be free of charge, whereas other applications may be purchased or obtained through a subscription.

In the example illustrated, while the custom application 54 is residing on the Web server or will prior to the custom application being distributed to a particular customer (even though the custom map occasion may have been previously distributed to prior customers), provider 128 has the ability to update, such as by upgrading or downgrading the authorization level or authorization key for the custom application 54. For example, during actual use of the custom application 54, it may be discovered or determined that prior concerns regarding custom application 54 are not warranted or are less severe, justifying the upgrading of the authorization level or authorization key to allow custom application 54 greater access to hardware 26 and/or data 56. In other circumstances, it may be later discovered determine that there exists additional concerns regarding safety, reliability, performance and the like that justify a downgrade of youth authorization level or authorization key to restrict access to hardware 26 and/or data 56 to a greater extent. After an authorization key or authorization level of the custom application 54 has been changed, new downloads or new acquisitions of custom application 54 one have been newly assigned authorization key or authorization level. In one implementation, provider 128 may further maintain a database keeping track of those customers who have downloaded or acquired custom application 54 with the former authorization key or authorization level and those customers who have download or acquired custom application 54 with the new updated authorization key or authorization level. As a result, provider 128 manages what percentage of users have an updated custom application 54 with a new authorization level. If circumstances warrant, provider 128 may contact customers recommending that they download or obtain more recent version of the custom application 54 with the new authorization level or authorization key.

Figure 6:
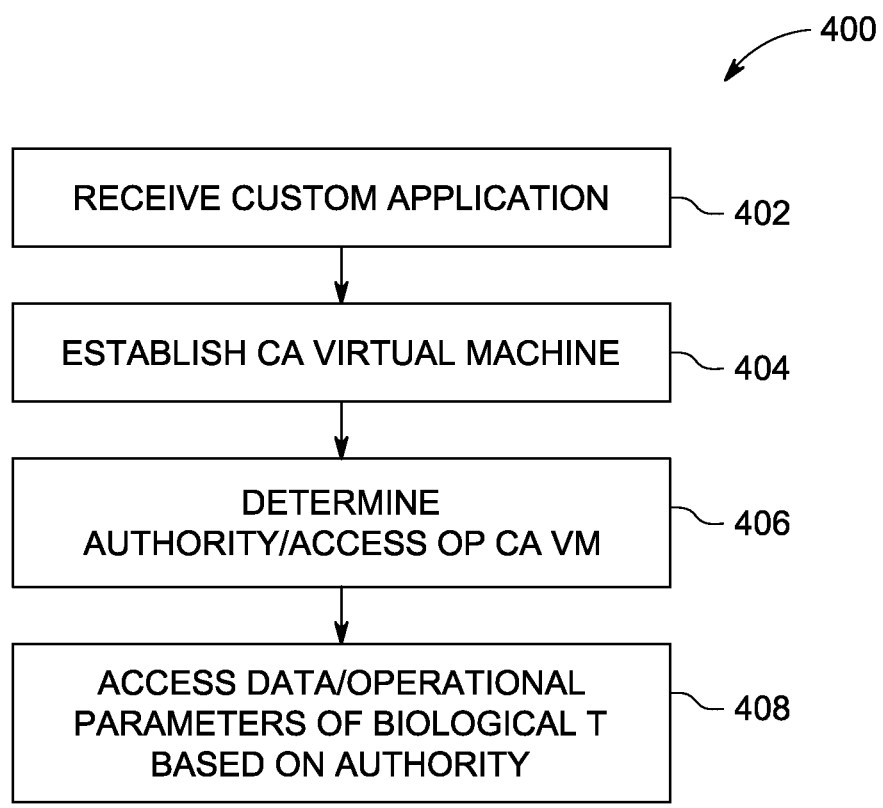
FIG. 6 is a flow diagram of an example method for carrying out a custom application in the system of FIG. 2.

FIG. 6 is a flow diagram of an example method 400 that may be executed by 120 for carrying out a custom application that has been installed on medical device 24. As indicated by step 402, medical device 24 receives the custom application from remote server 130 or from another computing device which has obtained the custom application from remote server 130. The received custom application is stored in memory 42 (custom application code 54).

As indicated by step 404, upon receiving a command or input through input 38 that the custom application is to be run or carried out, processor 44, following instructions of virtual machine code 50, creates virtual machine manager 32 and further implements or establishes a custom application virtual machine 30 for the received custom application.

As indicated by step 406, virtual machine manager 32 determines the level of authority or access of the custom application virtual machine. In particular, the custom application virtual machine 30 provides virtual machine manager 32 with the encrypted authorization key AK associated with the custom application. Virtual machine manager 30 decrypts or decodes the authorization key and utilizes the decoded authorization key credentials to determine what authority or access of the particular custom application and its custom application virtual machine has with respect to hardware 26 and base data 56.

As indicated by step 408, once the authority level has been determined, virtual machine manager 32 regulates access to hardware 26 and base data 36 by custom application virtual machine 30 in accordance with the defined authority level. For example, if the custom application has an associated authorization key AK6, virtual machine manager 32 allows the custom application virtual machine 30 to access and utilize processor 40 only when the biological probe 26 is dormant. If the custom application has an associated authorization key AK3, virtual machine manager 32 permits the virtual machine 30 to access a selected subset of base data 36. If the custom application has an associated authorization key AK8, the virtual machine manager 32 permits a virtual machine 30 to access and alter one or more selected operational parameters of medical device 24.

Figure 7:
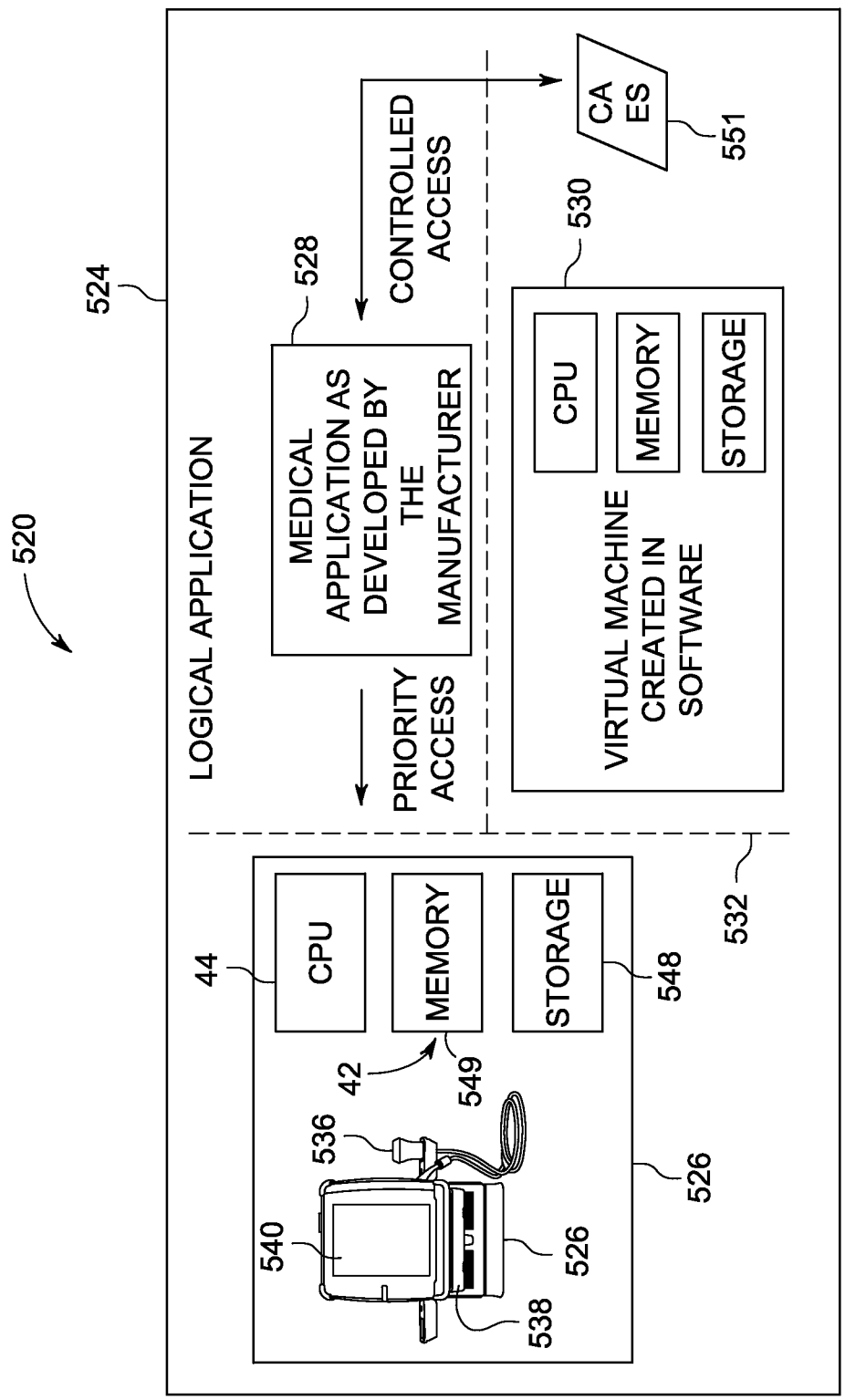
FIG. 7 is a schematic diagram of another example medical device customization system.

FIG. 7 schematically illustrates medical device customization system 520, an example implementation of system 20. System 520 comprises medical device 524. In one implementation, system 520 may additionally comprise one or more of developer/customers 122, 124, medical device provider 128 and remote server 130 (described above with respect to system 120). Similar to medical device 24, medical device 524 comprises physical hardware 526, base application virtual machine 528, custom application virtual machine 530 and virtual machine manager 532.

Physical hardware 526 comprises the electronic hardware of medical device 524 which is utilized by base application virtual machine 528 and at least sometimes by custom application virtual machine 530. Physical hardware 526 comprises biological probe 536, input 538, display 540, memory 542 and processing unit 544.

Biological probe 536 comprises a device that interacts with a patient to sense one or more biological characteristics of the patient. In the example implementation illustrated, biological probe 36 merely senses such characteristics without affecting or impacting such characteristics. In the example illustrated, biological probe 36 comprises an ultrasound probe. In other implementations, biological probe 36 may sense such biological characteristics of the patient as the patient is operated upon using the medical device, wherein the biological probe 36 provides feedback during surgery or operation.

Input 538 comprises a component of medical device 524 by which selections, commands or instructions are input to medical device 24. In the example illustrated, input 538 comprise a keyboard. In other implementations, input 538 may comprise a touchpad, a touch screen, a keypad, a keyboard, a mouse, a stylus, a microphone with speech recognition software, pushbuttons, slider bars and the like. In one implementation, input 38 may comprise a port for connection to a wired connection to an external input device or a wireless card or antenna for a wireless connection to an external input device. In some implementations, input 38 may be omitted.

Display 540 comprises a component of medical device 524 by which the data (raw or processed) from or based upon signals from biological probe 36 may be output or presented to a caretaker or physician. In the example illustrated, display 540 comprises a screen or monitor. In one implementation, display 540 may comprise a touch screen, wherein display 540 also serves as input 538. In some implementations, display 40 is incorporated as part of the body or housing of medical device 24. In another implementation, display 40 is a separate unit connected to or in communication with processing unit 544. In yet another implementation, display 540 may be omitted or may be separately provided as part of an independent electronic device, such as a personal data assistant, tablet, IPAD, IPOD or other external device connected to or in communication with medical device 524.

Memory 542 comprises one or more non-transient computer-readable mediums or persistent storage devices by which computer readable programs or code and data may be stored and accessed. Memory 42 comprises data storage portion 548 and code storage portion 549 for storing virtual machine code 50, base application code 52 and custom application code 54 described above respect to medical device 24). Data storage portion 548 comprise that portion of memory 542 reserved for storing base data 56 (described above).

Processing unit 544 comprises one or more processing units per carry out instructions contained in virtual machine code 50, base application code 52 and custom application code 54 to generate and operate base application virtual machine 528, custom application virtual machine 530 and virtual machine manager 532. Base application virtual machine 528 comprises an isolated operating system installation implemented through software or hardware virtualization. Base application virtual machine 528 comprises an application virtual machine, running as a normal application inside the host operating system of medical device 528 and supporting or carrying out base processes of medical device 528 according to base application code 552. For example, base application virtual machine 528 controls the operational parameters for biological probe 536. Base application virtual machine 528 processes signals from biological probe 528 and controls the storage of such raw data signals from biological probe 536 in storage portion 548 of memory 542. Base application virtual machine 528 may further process and analyze such signals from biological probe 536 to store additional data derived from such signals in storage portion 548 of memory 542. Base application virtual machine 528 further controls the display of data on display 540 and user interfaces for the control of biological probe 536 and display 540 through input 538. For example, base application virtual machine 528 may control how data is presented or what format is used when presenting data or other information on display 540 or what graphical user interfaces or icons are presented on a touch screen of input 538. Base application virtual machine 528 has unlimited access to hardware 526 and data stored in memory 542.

Custom application virtual machine 30 comprises an isolated operating system installation implemented through software or hardware virtualization. Custom application virtual machine 530 comprises an application virtual machine, running as a normal application inside the custom map patient executable space 551 of medical device 524 and supporting or carrying out base processes of medical device 524 according to custom application code 54. Custom application virtual machine 430 provides additional features or modifies operation of medical device 524 according to an end user's objectives. For example, custom application virtual machine 530 may provide further processing or analysis of the base data 56 stored by base application virtual machine 528 in storage portion 548 of memory 542, providing or forming new post processing data or new conclusions derived from base data 56. Custom application virtual machine 530 may also provide different formats (presentation styles, screen layouts, graphs, color coding and the like) for the output of base data 56. In some implementations, custom application virtual machine 530 may alter the operational parameters of biological probe

536, altering the settings for transducer 536 or driving transducer 536 to obtain additional measurements. Custom application virtual machine 30 provides customized operation of medical device 524. In one implementation, virtual machines 528, 530 are implemented with JAVA programming language employing a JAVA virtual machine.

Virtual machine manager 532, sometimes referred to as a hypervisor, manages the execution of base application virtual machine 528 and custom application virtual machine 530. Virtual machine manager 532 is operates according to virtual machine code 50 and serves as an interpreter implementing base application virtual machine 528 and custom application virtual machine 530. Virtual machine manager 532 manages utilization of and access to various components of hardware 526 and base data 56 by virtual machines 528, 530.

Because custom applications defined by custom application code 54 operate through virtual machine 530, system 520 may be updated or customized to accommodate new and different environments, user demands, and advances. At the same time, because virtual machine 530 implements such customization, system 520 may offer such customization while maintaining integrity of the original base application and the original (potentially FDA approved) operation of medical device 524 and biological probe 536. In other words, the risk that a custom application may undesirably alter the original intended operation of medical device 528 or may undesirably destroy or alter based data 56 is reduced.

In the example illustrated in FIG. 7, the actual medical application 528 always has priority access to physical hardware 526. Although the virtual machine 530 does not have any physical hardware of its own, is virtualized appears a separate physical resource, permitting certified custom created application to execute through the virtual machine 530. Integrity of hardware 526 and of data 56 is maintained since such custom application execute only through allowed pathways to the actual medical application. The separation between the physical and virtual provides protection to the actual medical device.

Although the present disclosure has been described with reference to example embodiments, workers skilled in the art will recognize that changes may be made in form and detail without departing from the spirit and scope of the claimed subject matter. For example, although different example embodiments may have been described as including one or more features providing one or more benefits, it is contemplated that the described features may be interchanged with one another or alternatively be combined with one another in the described example embodiments or in other alternative embodiments. Because the technology of the present disclosure is relatively complex, not all changes in the technology are foreseeable. The present disclosure described with reference to the example embodiments and set forth in the following claims is manifestly intended to be as broad as possible. For example, unless specifically otherwise noted, the claims reciting a single particular element also encompass a plurality of such particular elements.

What is claimed is:

1. A medical device customization system comprising:
    a medical device comprising:
        hardware comprising:
            a biological probe;
            a memory; and
            a processing unit to receive signals from the biological probe and to store data in the memory based on signals from the biological probe; and
        a virtual machine manager establishing:
            a base application virtual machine to process signals from the biological probe and store base data in the memory; and
            a custom application virtual machine for carrying out a custom application using the base data stored by the base application virtual machine in the memory, wherein the code directs the processing unit to determine the authority level based on an encrypted authorization key received from the custom application virtual machine.

2. The system of claim 1, wherein the virtual machine manager limits access to the hardware by the custom application carried out by the custom application virtual machine based on an authority level of the custom application.

3. The system of claim 2, wherein the authority level permits the custom application virtual machine to access the base data in the memory.

4. The system of claim 3, wherein the authority level limits a time at which the custom application virtual machine is permitted to access the base data to when the biological probe is dormant.

5. The system of claim 3, wherein the authority level limits access by the custom application virtual machine to a predefined subset of the base data in the memory.

6. The system of claim 3, wherein the authority level limits access to the base data in the memory to reading, but not altering the base data in the memory.

7. The system of claim 2, wherein the authority levels permit the virtual machine to alter operational parameters for the biological probe.

8. The system of claim 1 further comprising a server remote from the medical device, the server storing a plurality of custom applications for the medical device and making the applications available for download to the medical device.

9. The system of claim 8, wherein different custom applications are assigned a different authority level having a limitation selected from a group of limitations consisting of: limiting a time when the custom application virtual machine is permitted to access the base data to when the biological probe is dormant; limiting access by the custom application virtual machine to a predefined subset of the base data in the memory; and limiting access to reading base data in the memory, not altering base data in memory.

10. The system of claim 8, wherein the custom application developed by a developer has an authorization key encrypted by a provider of the medical device and undisclosed to the developer.

11. A method comprising:
    receiving signals from a biological probe having an operational parameter;
    storing base data based on the signals in a memory of a medical device under control of a base application virtual machine;
    receiving, by the medical device, a custom application;
    establishing a virtual machine on the medical device to run the custom application using the stored base data in the memory; and
    determining an authorization level for the virtual machine based on an encrypted authorization key.

12. The method of claim 11 further comprising limiting access to at least one of the base data and the operational parameter by the virtual machine based on the authorization level associated with the custom application.

13. The method of claim 12, wherein the authorization level limits a time at which the custom application virtual machine is permitted to access the base data to when the biological probe is dormant.

14. The method of claim 12, wherein the authorization level limits access by the virtual machine to a predefined subset of the base data in the memory.

15. The method of claim 12, wherein the authorization level limits access to the base data in the memory to reading, but not altering the base data in the memory.

16. The method of claim 12, wherein the authorization level permits the virtual machine to alter operational parameters for the biological probe.

17. The method of claim 11, wherein a virtual machine manager determines the authorization level based on the encrypted authorization key received from the virtual machine.

18. The method of claim 11 further comprising providing a repository of downloadable custom applications for the medical device.

19. The method of claim 18, wherein the repository is provided by provider the medical device, wherein a first one of the custom applications is provided with a first authority level by the provider and wherein a second one of the custom applications is provided with a second authority level by the provider different than the first authority level.

20. The method of claim 18, wherein a first one of the custom applications is provided by a first developer and wherein a second one of the custom applications is provided by second developer not associated with the first developer.

21. A medical device customization system comprising:
a server storing a plurality of custom applications for a medical device to making applications available for download to the medical device, wherein one of the custom applications is developed by a developer and has an encrypted authorization key indicating an authorization level for accessing hardware of the medical device, wherein the encrypted authorization key is encrypted by a provider of the medical device and wherein the authorization key is known only to the provider.

22. The system of claim 21, wherein a first one of the custom applications is provided with a first authority level by the provider for accessing at least one of raw data and operational parameters of the medical device and wherein a second one of the custom applications is provided with a second authority level by the provider different than the first authority level for accessing at least one of raw data and operational parameters of the medical device.

23. The system of claim 22, wherein the first authority level and the second authority level are indicated by encrypted authorization keys.

24. A medical device customization system comprising:
a medical device comprising:
hardware comprising:
a biological probe;
a memory; and
a processing unit to receive signals from the biological probe and to store data in the memory based on signals from the biological probe; and
a virtual machine manager establishing a virtual machine for carrying out a custom application, wherein the virtual machine manager limits access to the hardware by the custom application carried out by the virtual machine based on an authority level of the custom application, wherein the authority level is based on a received authorization key; and
a server remote from the medical device, the server storing a plurality of custom applications for the medical device, including the custom application, and making each of the plurality of custom applications available for download to the medical device, wherein each of the plurality of custom applications are assigned a different authority level having a limitation selected from a group of limitations consisting of: limiting a time when the custom application virtual machine is permitted is to access the base data to when the biological probe is dormant; limiting access by the custom application virtual machine to a predefined subset of the base data in the memory; and limiting access to reading base data in the memory, not altering base data in memory.

* * * * *